(12) United States Patent
Matsuo et al.

(10) Patent No.: US 7,540,878 B2
(45) Date of Patent: Jun. 2, 2009

(54) THERMOTHERAPY DEVICE

(76) Inventors: Atsushi Matsuo, c/o Kobayashi Pharmaceutical Co., LTD. R&D Company 30-3, Toyokawa 1chome, Ibaraki-shi, Osaka 5670057 (JP); Shuichi Yoshikawa, c/o Kobayashi Pharmaceutical Co., LTD. R&D Company 30-3, Toyokawa 1chome, Ibaraki-shi, Osaka 5670057 (JP); Yuka Kitamoto, c/o Kobayashi Pharmaceutical Co., LTD. R&D Company 30-3, Toyokawa 1chome, Ibaraki-shi, Osaka 5670057 (JP)

( * ) Notice: Subject to any disclaimer, the term of this patent is extended or adjusted under 35 U.S.C. 154(b) by 519 days.

(21) Appl. No.: 11/325,630

(22) Filed: Jan. 5, 2006

(65) Prior Publication Data

US 2006/0173519 A1    Aug. 3, 2006

Related U.S. Application Data

(63) Continuation of application No. PCT/JP2004/009549, filed on Jul. 6, 2004.

(30) Foreign Application Priority Data

Jul. 7, 2003   (JP)   ............................. 2003-271648

(51) Int. Cl.
*A61F 7/12*   (2006.01)
(52) U.S. Cl. .................. 607/96; 607/108; 607/112; 607/114
(58) Field of Classification Search ............ 607/96–114
See application file for complete search history.

(56) References Cited

U.S. PATENT DOCUMENTS 4,575,097 A * 3/1986 Brannigan et al. .......... 607/112

(Continued)

FOREIGN PATENT DOCUMENTS

| JP | 1-44746 | 9/1989 |
| JP | 11-508785 | 8/1999 |

(Continued)

*Primary Examiner*—Roy D Gibson
*Assistant Examiner*—Kaitlyn E Helling
(74) *Attorney, Agent, or Firm*—Kratz, Quintos & Hanson, LLP

(57) ABSTRACT

A thermotherapy device has a plurality of heat generation portions disposed on a flexible band-like body, the heat generation portions each comprising a base sheet and an oxygen permeable sheet forming the flexible band-like body, a bag-like accommodation portion formed between the base sheet and the oxygen permeable sheet, and a composition that generates heat filled in the accommodation portion, wherein the filling ratio R satisfies expression (1) below and is less than 0.7, and the heating value of the exothermic composition is not less than 0.26 kcal/cm² per planar area of the accommodation portion:

$$R \leq -0.016S + 0.94 \quad (1)$$

wherein S is the planar area of the accommodation portion of the exothermic composition (unit: cm²), and R is defined by the following expression:
R=(mass of the exothermic composition in the accommodation portion)/(maximum mass of the exothermic composition that can be filled in the accommodation portion).

8 Claims, 6 Drawing Sheets

U.S. PATENT DOCUMENTS

| | | | |
|---|---|---|---|
| 4,981,135 A * | 1/1991 | Hardy | 607/108 |
| 5,674,270 A * | 10/1997 | Viltro et al. | 607/112 |
| 5,728,146 A * | 3/1998 | Burkett et al. | 607/109 |
| 5,918,590 A * | 7/1999 | Burkett et al. | 126/263.02 |
| 6,020,040 A * | 2/2000 | Cramer et al. | 428/64.1 |
| 6,074,413 A * | 6/2000 | Davis et al. | 607/112 |

FOREIGN PATENT DOCUMENTS

| | | |
|---|---|---|
| JP | 11-508786 | 8/1999 |
| JP | 2002-512539 | 4/2002 |
| JP | 2002-514103 | 5/2002 |
| WO | 97/01312 | 1/1997 |
| WO | 97/01313 | 1/1997 |
| WO | 98/29065 | 7/1998 |
| WO | 98/29067 | 7/1998 |

* cited by examiner

THERMOTHERAPY DEVICE

This application is a continuation of international application PCT/JP04/09549 filed Jul. 6, 2004.

BACKGROUND OF THE INVENTION (1) Field of the Invention

The present invention relates to a thermotherapy device effective in alleviating pains of various parts of the body, such as stiffness of the shoulders, backache, etc.

(2) Description of Related Art

Thermotherapy, which applies heat to the afflicted area, is one of the methods for alleviating pains of various parts of the body, such as stiffness of the shoulders. Such thermotherapy typically uses heat produced by an exothermic composition which comprises iron powder and a pro-oxidant and is accommodated in a bag. Such an exothermic composition, whose temperature is controlled to about 45° C., and is capable of maintaining the skin-temperature, for a predetermined period of time, within a range of about 38 to about 42° C. suitable for treating the afflicted area. Exothermic compositions are hence widely used in thermotherapy devices.

Conventional thermotherapy devices using such an exothermic composition, in general, comprise a single heat generation portion having an exothermic composition accommodated in a bag of a particular size. Such thermotherapy devices of the type having a single heat generation portion are known to work effectively for the purpose of intensively treating a single afflicted area. However, when a large thermotherapy device is attached to a rather long, broad part of the body for treating stiff shoulders, backache or the like, this may result in warming not only the muscles but also bones in deep region, inhibiting the intended treatment from being effectively applied. Moreover, when such a heat generation portion has excessively large area, it does not easily fit on onto curved parts of the body, such as the shoulders.

As such a thermotherapy device, for example, Patent Document 1 discloses a heat cell filled with a granular exothermic composition containing predetermined amounts of iron powder, activated carbon, metal salt, and water, wherein the ratio of the fill volume to the cell volume is 0.7 to 1.0, and the thickness of the heat cell is 0.15 to 1.0 cm. Further, Patent Document 2 teaches a thermotherapy device for the neck (thermal neck wrap) comprising a substantially triangular piece of flexible material, and a plurality of individual thermal elements (heat generation portions) embedded and fixed therein. The respective thermal elements of the thermal neck wrap correspond to the muscles in the user's upper back, lower neck, shoulders and the like to warm such parts of the body.

In each of the thermotherapy devices disclosed in the aforementioned Patent Documents 1 and 2, the heat generation portion or each heating element has limited dimensions such that it fits along a curved part, such as the neck. However, these heat generation portions, depending on where they are attached, fit poorly along body surfaces, and therefore do not necessarily achieve sufficient thermotherapy effects.

Patent Document 1: Japanese translation of PCT international application No. 11-508786 (WO97/01313)
Patent Document 2: Japanese translation of PCT international application No. 11-508785 (WO97/01312)

SUMMARY OF THE INVENTION

An object of the present invention is to provide to a band-like thermotherapy device that fits well onto the human body and is effective in alleviating pains of various parts of the body, such as stiffness of the shoulders, backache, etc.

The object of the present invention can be achieved by a thermotherapy device (1) comprising a plurality of heat generation portions disposed on a flexible body, having a form of a band, the plurality of the heat generation portions each comprising a base sheet and an oxygen permeable sheet that also form the flexible body, an accommodation portion formed between the base sheet and the oxygen permeable sheet and having a form of a bag, and a exothermic composition that generates heat when oxidized filled in the accommodation portion, wherein the filling ratio R of the exothermic composition in the accommodation portion satisfies the expression below and is less than 0.7:

$R \leq -0.016S + 0.94$ wherein S is the planar area of the accommodation portion of the exothermic composition expressed in $cm^2$, and R is defined by the following expression:
R=the ratio of the mass of the exothermic composition in the accommodation portion to the maximum mass of the exothermic composition that can be filled in the accommodation portion; and the heating value of the exothermic composition in the accommodation portion is not less than 0.26 $kcal/cm^2$ per planar area of the accommodation portion.

An object of the present invention can also be achieved by a thermotherapy device (2) of the present invention according to the thermotherapy device (1), which has a filling ratio R of not greater than 0.63.

An object of the present invention can also be achieved by a thermotherapy device (3) of the present invention according to the thermotherapy device (1), which has a filling ratio R of not greater than 0.45.

An object of the present invention can also be achieved by a thermotherapy device (4) of the present invention according to the thermotherapy devices (1), wherein the flexible body has a shape in the form of a flat U corresponding to the shapes of rhomboid muscle areas, trapezius muscle areas and scapular muscle areas of the right and left shoulders, and the flexible body comprises at least four heat generation portions.

An object of the present invention can also be achieved by a thermotherapy device (5) of the present invention according to the thermotherapy devices (1), wherein the flexible body has a shape in the form of a flat L corresponding to the shapes of rhomboid muscle area, trapezius muscle area or scapular muscle area of a shoulder, and the flexible body comprises at least two heat generation portions.

An object of the present invention can also be achieved by a thermotherapy device (6) of the present invention according to the thermotherapy device (4), wherein the heat generation portions are disposed so as to correspond to the rhomboid muscle areas, trapezius muscle areas and scapular muscle areas.

An object of the present invention can also be achieved by a thermotherapy device (7) of the present invention according to the thermotherapy device (5), wherein the heat generation portions are disposed so as to correspond to the rhomboid muscle areas, trapezius muscle areas and scapular muscle areas.

An object of the present invention can also be achieved by a thermotherapy device (8) of the present invention according to the thermotherapy devices (1), wherein the flexible body has a shape having a form of a band and comprises at least two heat generation portions.

In the thermotherapy device (1) according to the present invention, the filling ratio satisfies the aforementioned expression (1) and is also determined to be less than 0.7. The thermotherapy device (1), therefore, fits excellently onto a human body. Providing an excellent fit also means being capable of effectively transferring heat to the afflicted area. Further, the lower limit of the amount of heat generation from the exothermic composition is set according to the area of the accommodation portion. The thermotherapy device is thus capable of maintaining the afflicted area at a predetermined temperature over a sufficient period of time. Consequently, the thermotherapy device (1) is an excellent therapeutic device which satisfies both the feeling when used and the heating effects.

In each of the thermotherapy devices (2) and (3) according to the invention, the upper limit of the filling ratio is defined, so that the device achieves an excellent fit and treating effects as a thermotherapy device for use on the shoulders and the lower back.

In the thermotherapy device (4) according to the invention, the flexible band-like body has a flattened U-shape corresponding to the rhomboid muscle areas, trapezius muscle areas, and scapular muscle areas in the shoulders, and comprises at least four heat generation members. This results in excellent effects for thermotherapy of the shoulders, in particular.

In the thermotherapy device (5) according to the invention, the flexible band-like body is shaped so as to fit along a shoulder, resulting in excellent effects for thermotherapy of only one of the shoulders.

In the thermotherapy device (6) or (7) according to the invention, the heat generation portions are disposed so as to correspond to the rhomboid muscle areas, trapezium muscle areas, and scapular muscle areas in the shoulders, result in effective thermotherapy of these muscles.

In the thermotherapy device (8) according to the invention, the flexible band-like body has a substantially band-like shape, resulting in excellent effects for thermotherapy of the lower back, in particular.

BRIEF DESCRIPTION OF THE DRAWINGS

FIGS. 1A and 1B show an example of a thermotherapy device according to an embodiment of the present invention wherein

FIGS. 5A to 5D are a plan view of the thermotherapy device used in examining the fit to the body surface, wherein FIG. 5A shows the case where its accommodation portion is not divided, FIG. 5B shows the case where its accommodation portion is divided into two, FIG. 5C shows the case where its accommodation portion is divided into four, and FIG. 5D shows the case where its accommodation portion is divided into six;

FIGS. 8A and 8B are a plan view showing thermotherapy devices according to another embodiment of the present invention wherein FIG. 8A shows an example of a thermotherapy device suitable for treating one of shoulder, and FIG. 8B shows an example of a thermotherapy device suitable for treating the lower back;

FIG. 9 is a side view schematically showing the structure of equipment for manufacturing the thermotherapy device of FIGS. 1A and 1B;

FIGS. 10A to 10C are diagrams illustrating the method for filling the exothermic composition in heat generation portions of the thermotherapy device, wherein FIG. 10A is a plan view showing a template and concave portions provided in the template, FIG. 10B is a development view of an upper drum showing the concave portions provided in the drum, FIG. 10C is a development view of a lower drum showing the condition in which the exothermic composition is adhered to the concave portions in the drum.

DETAILED DESCRIPTION OF THE INVENTION

With reference to the attached drawings, the thermotherapy device that is preferable for thermotherapy of parts with curves, such as the shoulder, lower back, etc., is described below in detail. In the drawings, the same or similar parts may be designated by the same reference numerals and a duplicate description omitted.

Figure 1A:
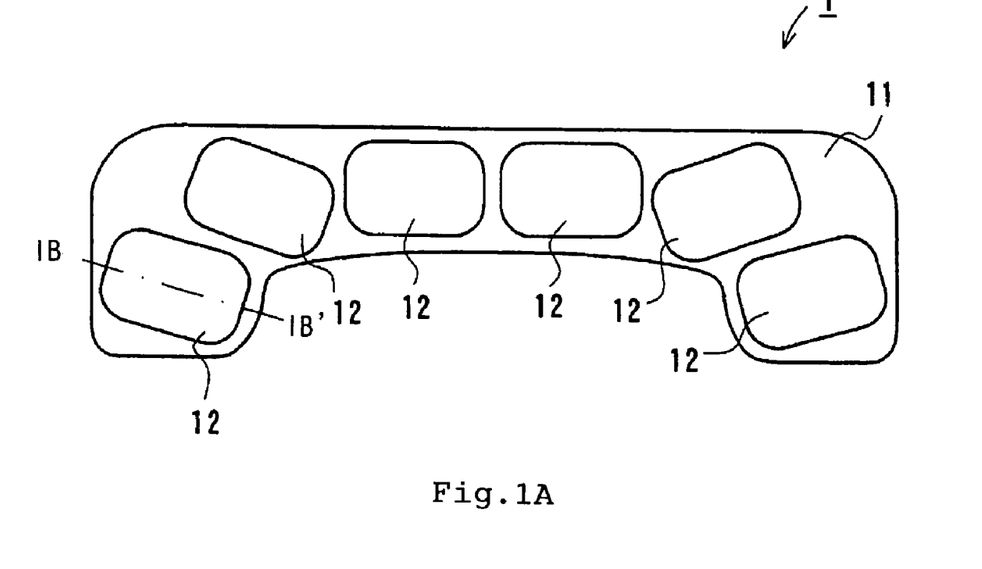
FIG. 1A is a plan view showing the entire thermotherapy device.
Figure 1B:
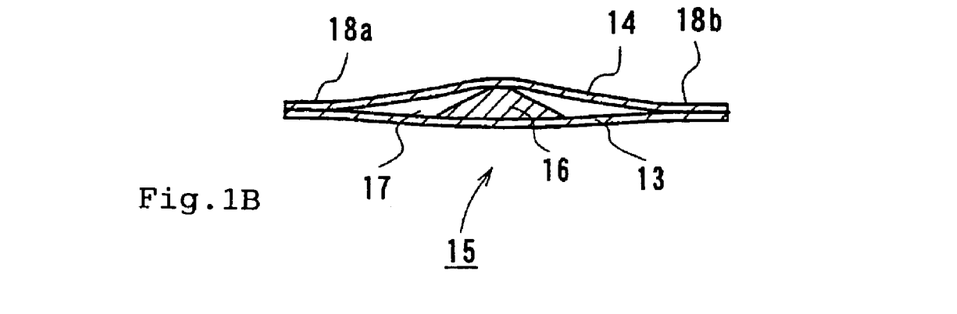
FIG. 1B is a schematic section view showing the cross-sectional structure of the thermotherapy device taken along the line IB-IB' in FIG. 1A.

FIGS. 1A and 1B are a set of drawings showing a thermotherapy device according to an embodiment of the present invention, in which FIG. 1A is a plan view showing the entire thermotherapy device, and FIG. 1B is a schematic section view showing the cross-sectional structure taken along line IB-IB' in FIG. 1A.

The thermotherapy device 1 shown in FIGS. 1A and 1B is an example of a thermotherapy device for the shoulder, and as shown in FIG. 1A, comprises six heat generation portions 12 disposed on a flexible band-like body 11. In the thermotherapy device 1, the flexible band-like body 11 has a flat U-shape so that the heat generation portions 12 come into contact with the rhomboid muscle area, trapezius muscle area and scapular muscle area of both shoulders. Further, six divided heat generation portions 12 are disposed on the flexible band-like body 11 so as to fit various portions of the shoulder with curves.

As shown in the cross-sectional structure illustrated in FIG. 1B, the flexible band-like body 11 comprises a base sheet 13 and an oxygen permeable sheet 14, and each of the heat generation portions 12 is formed of the base sheet 13, the oxygen permeable sheet 14, a bag-like accommodation portion 15 disposed between the base sheet 13 and oxygen permeable sheet 14, and an exothermic composition 16 filled in the accommodation portion 15. Each accommodation portion 15 is not completely filled with the exothermic composition 16, but has an unfilled portion 17 that does not contain the exothermic composition 16, as described hereinafter. Since the exothermic composition 16 is granular and has a certain degree of fluidity, the shape of the cavity (unfilled portion 17) varies with the flow of the exothermic composition 16. At outer peripheral portions 18a, 18b of each accommodation portion 15, the base sheet 13 and oxygen permeable sheet 14 are adhered to each other to avoid leakage of the granular exothermic composition 16.

Figure 2:
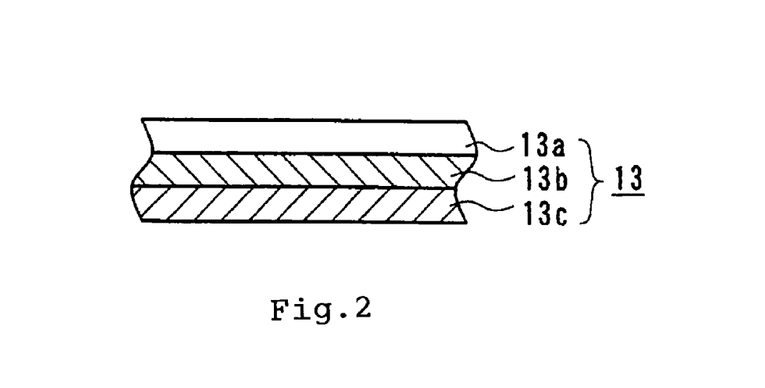
FIG. 2 is a section view showing a preferable example of the structure of a base sheet.

FIG. 2 is a section view showing a preferable example of the structure of the base sheet 13. The base sheet 13 is made of a material that is sufficiently flexible to fit the curves of the back shoulder or like body parts. The base sheet 13 may consist of a single layer of polyethylene, polypropylene, a polyethylene-polypropylene copolymer, a nylon-polyethylene copolymer or the like. Preferably, as shown in FIG. 2, the base sheet 13 comprises a support layer 13a made of opaque polyethylene, polyethylene, polypropylene or the like for supporting the exothermic composition 16; an adhesive layer 13b made of an acrylic resin, gum resin or the like for adhesion to the skin; and a releasing paper 13c for covering the adhesive layer 13b until the thermotherapy device 1 is used. Preferable components of the adhesive layer 13c include polyethylene, paper, silicone, polypropylene, polyethylene terephthalate, etc. The base sheet 13 need not be permeable to oxygen, and may be made of an airtight material.

Figure 3:
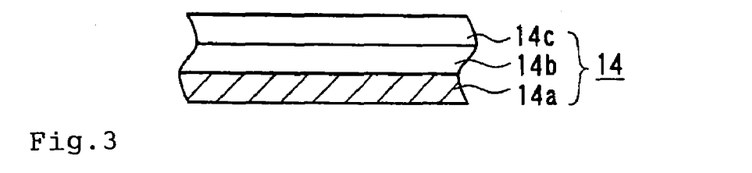
FIG. 3 is a section view showing a preferable example of the structure of an oxygen permeable sheet.

The oxygen permeable sheet 14 has flexibility and comprises a woven or nonwoven fabric having permeability to oxygen in the air, which is necessary for the oxidation reaction of the exothermic composition 16. Preferable woven or nonwoven fabrics include those of nylon, rayon, polyester, cellulose, cotton, hemp, silk, wool, viscose rayon, acrylic vinylon, polypropylene, acetate, glass fiber, polyurethane, etc. The oxygen permeable sheet 14 may consist of a single layer of such a material, or may comprise, as shown in FIG. 3, a nylon nonwoven fabric 14a and a porous polyethylene layer 14c adhered to the nylon nonwoven fabric 14a via an air-permeable adhesive layer 14b. In this case, the porous polyethylene layer 14c has the effects of adhering the oxygen permeable sheet 14 to the base sheet 13 and controlling the amount of oxygen passing through the oxygen permeable sheet 14. A woven or nonwoven fabric of rayon, polyester, cellulose, cotton, hemp, silk, wool, viscose rayon, acryl vinylon, polypropylene, acetate, glass fiber, polyurethane or the like as mentioned above can be used in place of the nylon nonwoven fabric 14a, and a porous layer of polypropylene, a polyethylene-polypropylene copolymer, a nylon-polyethylene copolymer or the like may be used in place of the polyethylene porous layer.

The exothermic composition 16 is a composition which generates heat when oxidized and which is used in conventional thermotherapy devices. The composition comprises, in percentage by mass, 30 to 80% iron powder, 3 to 25% activated carbon, non-activated carbon or a mixture thereof, 0.5 to 10% metal salt such as alkali metal, alkaline earth metal or the like, 1 to 40% water, etc. Exothermic compositions having formulations other than the above can be used as long as they react with oxygen in the air and generate heat.

The exothermic composition 16 is not limited in grain size, and preferably contains at least 50% by mass of grains with a diameter of 53 μm or greater, so as to enable the heat generation portions 12 to fit the body well and to achieve a predetermined heat generating rate and heat generating time.

In the thermotherapy device 1 according to this embodiment of the present invention, as mentioned above, the relation between the filling ratio R of the exothermic composition 16 in each accommodation portion 15 and the planar area S (unit: cm$^2$) of the accommodation portion 15 is determined by the following expression (1). Further, R is less than 0.7.

$$R \leq -0.016S + 0.94 \tag{1}$$

wherein R is defined by the following expression:
R=(mass of the exothermic composition in the accommodation portion)/(mass of the exothermic composition that can be filled in the accommodation portion)

The "mass of the exothermic composition that can be filled in the accommodation portion" means the maximum mass of the exothermic composition 16 that can be placed in the accommodation portion 15 using vibration, oscillation or the like.

Expression (1) is a conditional expression obtained by a search by the present inventors for conditions that make the thermotherapy device 1 best fit uneven and curved portions of the body surface, such as the shoulder, lower back and the like. Expression (1) is derived based on the following.

Figure 4:
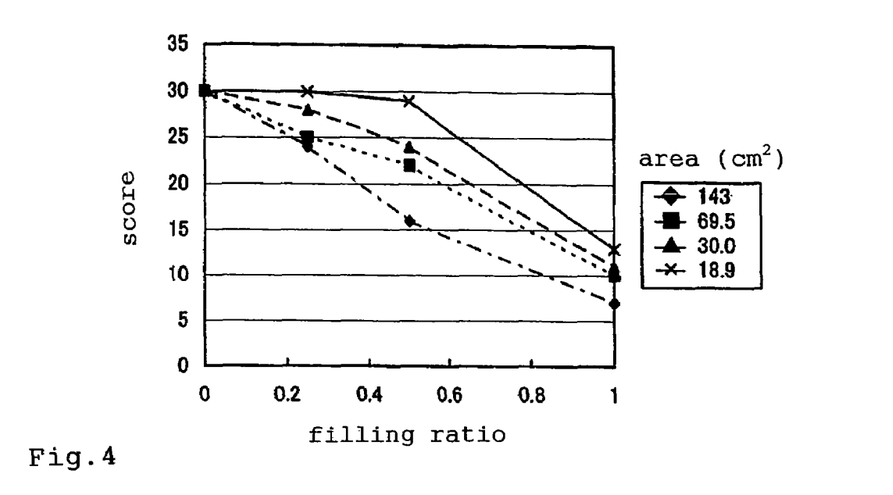
FIG. 4 is a graph showing the relation between the filling ratio R of the exothermic composition and the fit to the body surface.
Figure 5A:
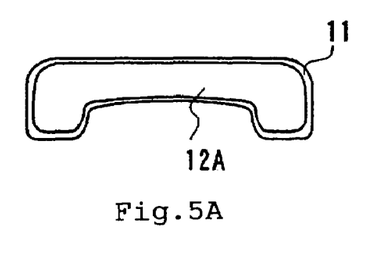
Figure 5B:
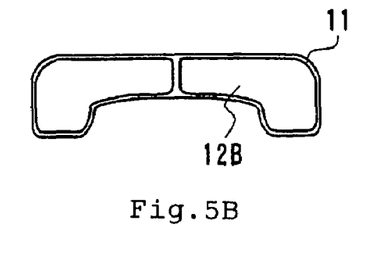
Figure 5C:
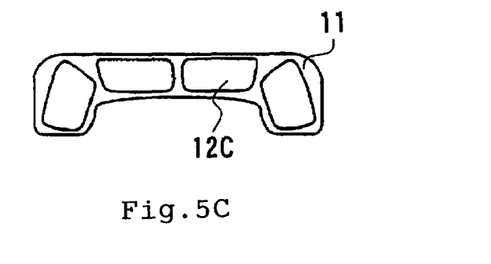
Figure 5D:
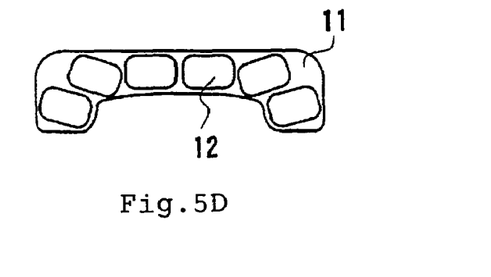

FIG. 4 is a graph showing the relation between the filling ratio R of the exothermic composition 16 and the fit to the body surface. This graph shows the investigation results that form the basis for expression (1). The thermotherapy device samples used in the investigation have the same overall configuration as the thermotherapy device illustrated in FIG. 1A. The samples have different numbers of heat generation portions 12 as shown in FIGS. 5A to 5D to vary the planar area (hereinafter sometimes simply referred to as "area") of each accommodation portion from 18.9 to 143 cm$^2$. Further, the mass of the exothermic composition 16 in each accommodation portion of the samples is changed to vary the filling ratio from 0 (no exothermic composition) to 1.0 (filled with the exothermic composition to the maximum extent). In FIGS. 5A to 5D, FIG. 5A shows a sample comprising an undivided accommodation portion 15 with an area of 143 cm$^2$ (maximum filling amount: 90.4 g); FIG. 5B shows a sample comprising two divided accommodation portions each having an area of 69.5 cm$^2$ (maximum filling amount: 44.1 g); FIG. 5C shows a sample comprising four divided accommodation portions each having an area of 30.0 cm$^2$ (maximum filling amount: 19.0 g); and FIG. 5D shows a sample comprising six divided accommodation portions each having an area of 18.9 cm$^2$ (maximum filling amount: 12.0 g).

Six people evaluated the fit of these samples on a scale of 1 to 5. In this investigation, in order to evaluate only the fit, the exothermic composition 16 was used without generating heat and was maintained at room temperature.

Figure 6:
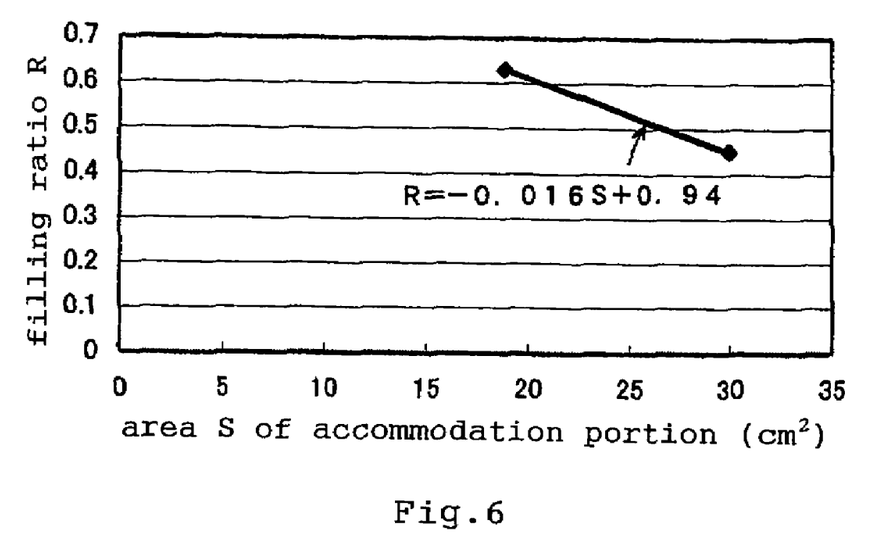
FIG. 6 is a graph showing the relation between the filling ratio and the area of the accommodation portion at a score of 25.

The ordinate of the graph shown in FIG. 4 represents the total of the scores obtained from the six people, and total scores of not less than 25 indicate a good fit. FIG. 6 is a graph showing the relation between the area S of each accommodation portion and filling ratio R, which corresponds to a total score of 25 in FIG. 4. The region on and below the straight line represented by expression (1) in FIG. 6 corresponds to conditions that achieve a good fit. Expression (1) indicates that a good fit can be obtained by lowering the upper limit of the filling ratio of the exothermic composition 16 in accordance with increase of the area of the accommodation portion 15.

Further, when expression 1 is satisfied and R is less than 0.7, the filling ratio of the exothermic composition 16 is limited so that the exothermic composition 16 flows easily and the heat generation portions 12 are highly flexible. The upper limit of the filling ratio of the exothermic composition 16 needs to be lowered in accordance with increase of the area of the accommodation portion 15, presumably because the increase of the area of the accommodation portions 15 reduces the area of the flexible band-like body 11 relative to the area of the accommodation portions 15, making it necessary for the heat generation portions 12 to be more flexible.

Figure 7:
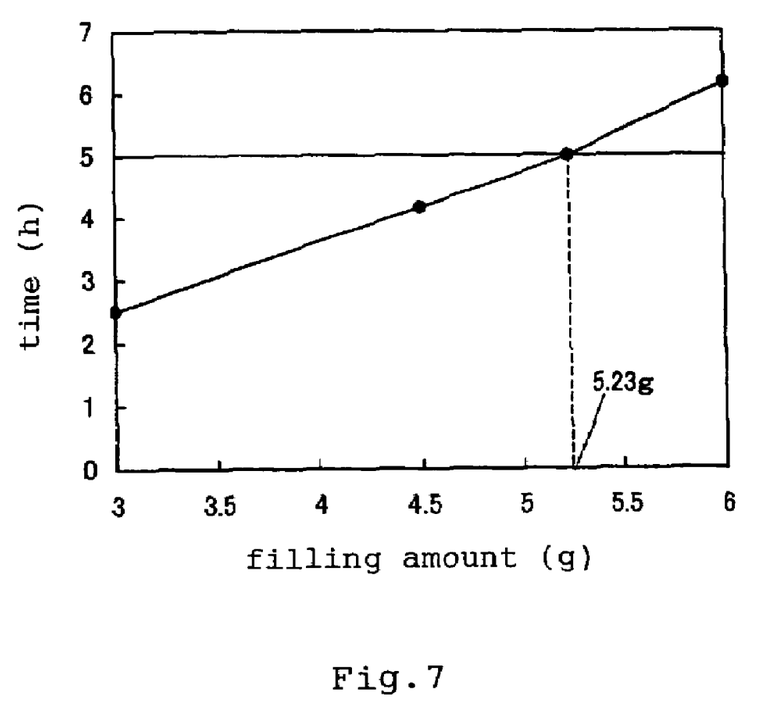
FIG. 7 is a graph showing the result of investigating the relation between the filling amount of the exothermic composition and the length of time that the skin temperature was maintained at about 40° C.

In the thermotherapy device 1 according to an embodiment of the present invention, the heating value of the exothermic composition 16 is not less than 0.26 kcal/cm$^2$ Generally, thermotherapy exhibits remarkable effects when the human skin temperature is maintained at 38 to 42° C. for five hours or more. FIG. 7 is a graph showing, in the case where the area of each accommodation portion 15 is 18.9 cm², the results of investigating the relation between the filling amount of the exothermic composition 16 and the length of time that the human skin temperature was maintained at about 40° C. It was confirmed from FIG. 7 that the filling amount of the exothermic composition that can maintain the human skin temperature at about 40° C. for five hours or more is 5.23 g. Since the heating value of the exothermic composition used in this investigation is 0.95 kcal/g, the above results revealed that the necessary heating value per unit area is 0.26 kcal/cm² (0.95×5.23/18.9) or more.

Exothermic compositions vary in heating value per unit mass depending on their formulation, and thus it is preferable to determine the filling amount of the exothermic composition having a heating value of 0.26 kcal/cm² or more, according to the formulation of the exothermic composition to be used.

The thermotherapy device 1 according to the embodiment shown in FIGS. 1A and 1B is a preferable example of a thermotherapy device for the shoulder, having a flat U-shape in its entirety and comprising six heat generation portions. In this type of thermotherapy device, the filling ratio of the exothermic composition in each accommodation portion 15 is not greater than 0.63, and the area of the accommodation portion 15 is about 19 cm².

A thermotherapy device according to another embodiment shown in FIG. 5C, which comprises four heat generation portions 12, is also preferable for the shoulder. In this case, the filling ratio of the exothermic composition 16 in each accommodation portion 15 is not greater than 0.45, and the area of the accommodation portion 15 is about 30 cm².

Figure 8A:
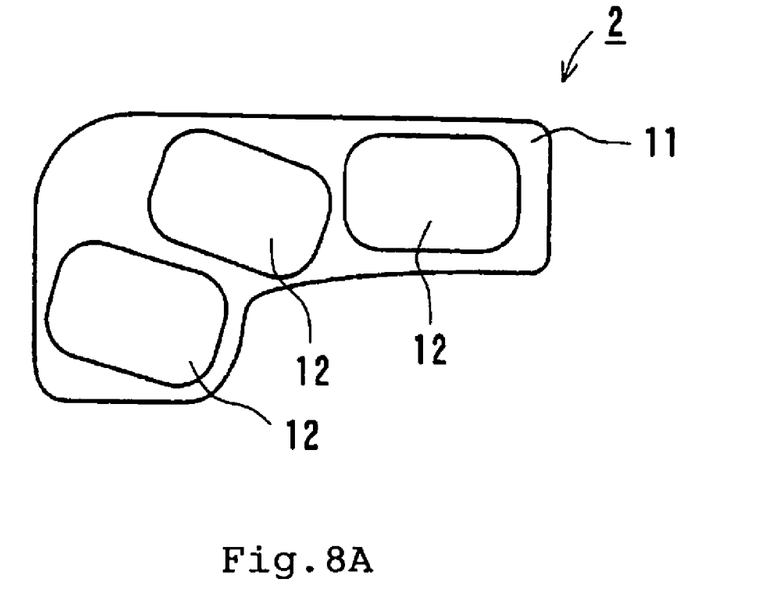
Figure 8B:
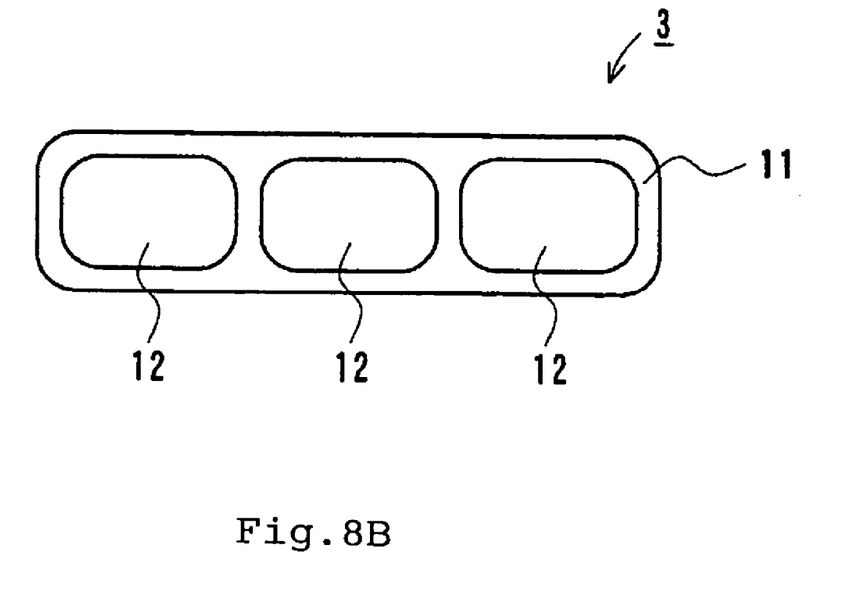

FIGS. 8A and 8B are a set of plan views showing thermotherapy devices according to still other embodiments, in which FIG. 8A shows an example of a thermotherapy device suitable for treating one of the shoulder, and FIG. 8B shows an example of a thermotherapy device suitable for treating the lower back. In both the thermotherapy device 2 with a flat L-shape for one of the shoulder and thermotherapy device 3 with a belt-like shape for the lower back, a plurality of heat generation portions 12 are provided, the filling ratio of the exothermic composition 16 satisfies expression (1) above, and the heating value of the exothermic composition 16 in the accommodation portions 15 is not less than 0.26 kcal/cm².

In the thermotherapy devices according to the above embodiments, the areas of the heat generation portions 12 need not be the same.

Figures 9, 10A, 10B, 10C:
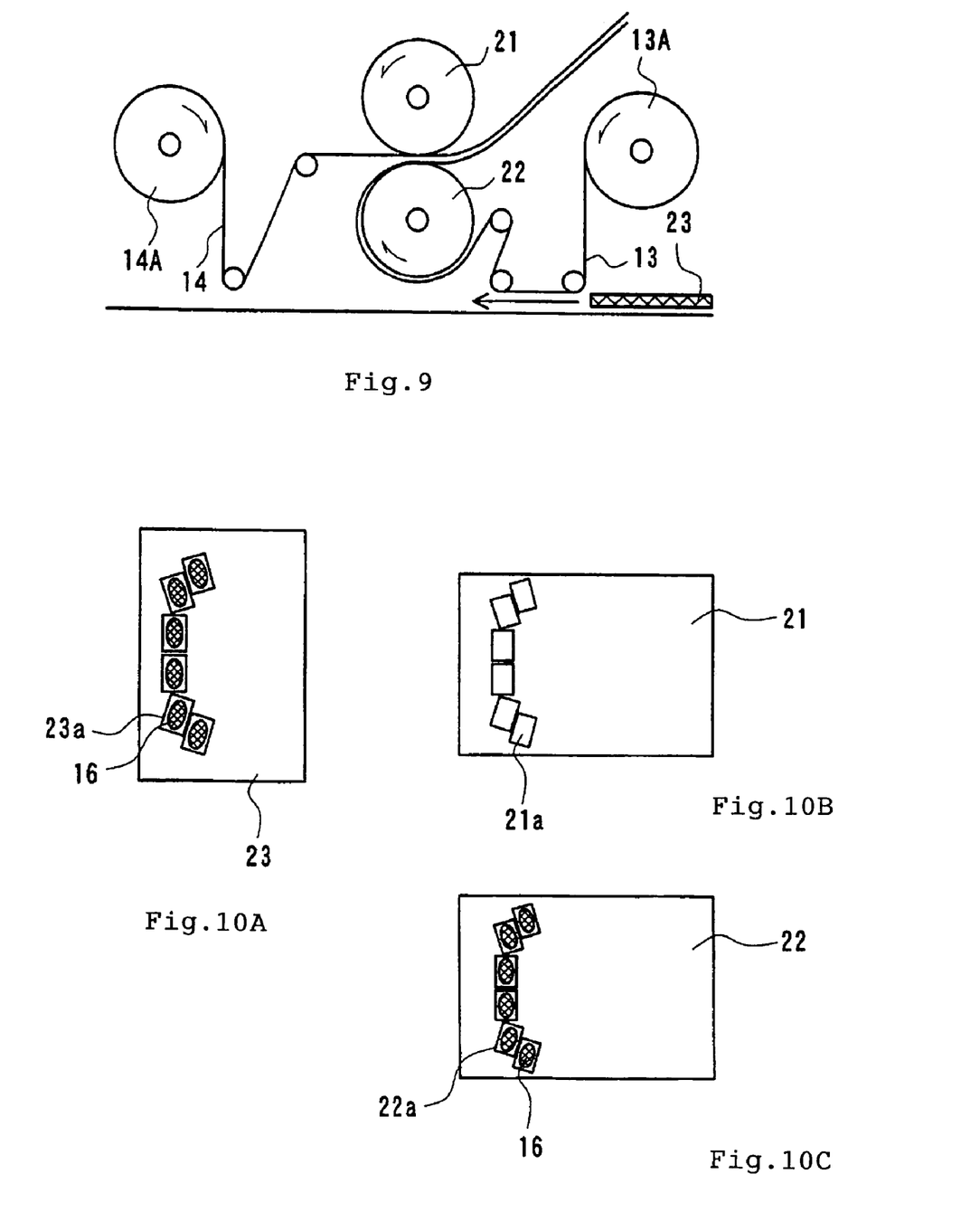

The above-described thermotherapy devices 1 to 3 can be manufactured, for example, by the following method. FIG. 9 is a side view schematically showing the structure of equipment for manufacturing the thermotherapy device of FIGS. 1A and 1B. The equipment comprises a pair of drums 21 and 22, and a base sheet 13 and an oxygen permeable sheet 14 are pressed between the two drums 21 and 22. The base sheet 13 and the oxygen permeable sheet 14 are supplied from a base sheet roll 13A and an oxygen permeable sheet roll 14A respectively. Both the drums 21 and 22 are heated to about 120° C. and the lower drum 22 magnetically adheres an exothermic composition 16 to the surface of the drum 22.

FIGS. 10A to 10C are diagrams illustrating the method for filling the exothermic composition 16 in heat generation portions 12 of the thermotherapy device 1, wherein FIG. 10A is a plan view showing a template 23 and concave portions 23a provided in the template 23, FIG. 10B is a development view of a drum showing the concave portions 21a provided in the upper drum 21, and FIG. 10C is a development view of a drum showing the condition in which the exothermic composition 16 is adhered to the concave portions 22a in the lower drum 22. In the drums 21 and 22, and in the template 23 shown in FIGS. 10A to 10C, concave portions 21a, 22a, and 23a each having the same area as the accommodation portion 15 are provided in the portions corresponding to the heat generation portions 12 of the thermotherapy device 1, wherein the locations of the concave portions 23a in the template 23 correspond to those of the concave portions 22a in the drum 22, and the concave portions 21a in the drum 21 face the concave portions 22a in the drum 22.

First, a predetermined amount of the exothermic composition 16 is placed in the concave portions 23a in the template 23, and the template 23 is passed to beneath the drum 22 covered with the base sheet 13. The exothermic composition 16, which is a magnetic substance, is attracted by the magnetic force of the drum 22 and adheres to the surface of the base sheet 13 in the concave portions 22a provided in the drum 22. Under this condition, the base sheet 13 and the oxygen permeable sheet 14 are heated by the drums 21 and 22 while being pressed between the drums 21 and 22. The base sheet 13 and the oxygen permeable sheet 14 are adhered to each other in the portions other than the concave portions 21a and 22a in the drums 21 and 22.

Figure 11:
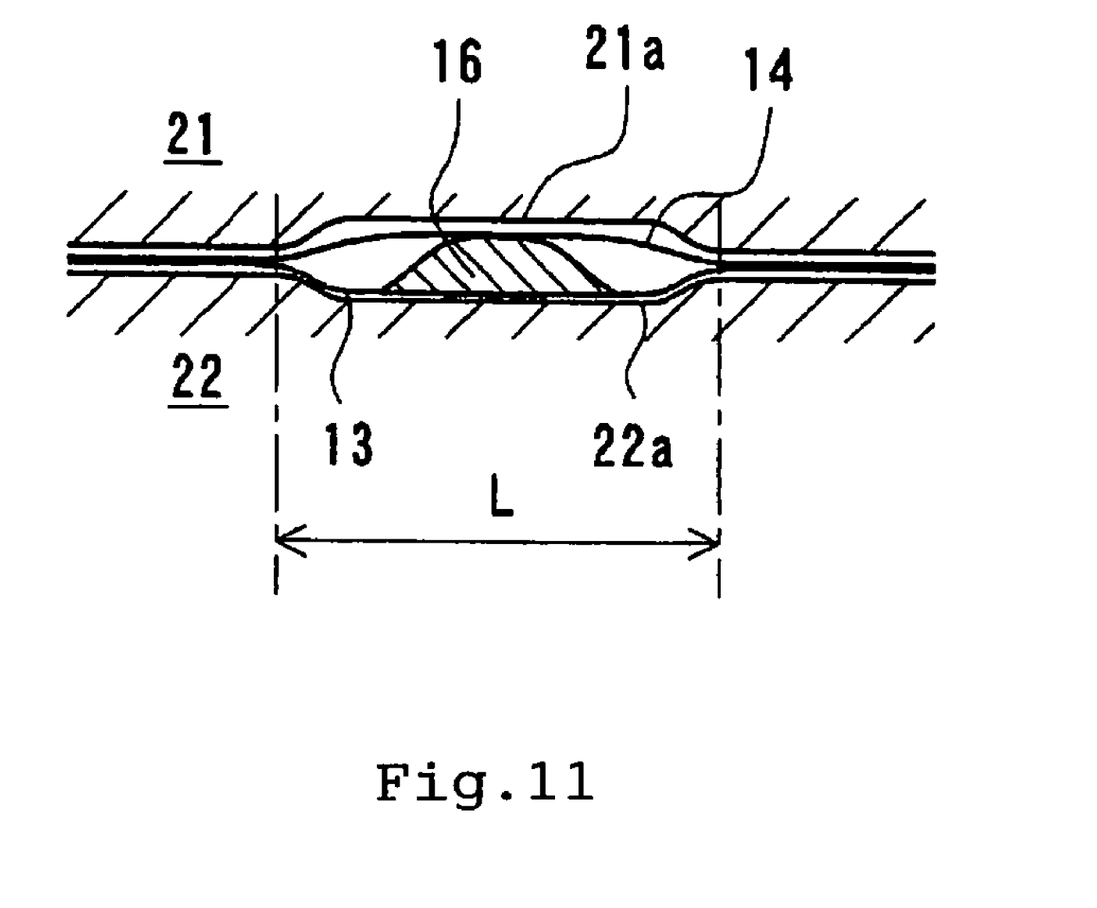
FIG. 11 is an enlarged section view showing the part in which heat generation portions are formed using drums.

FIG. 11 is an enlarged section view showing the part in which heat generation portions 12 are formed using a drum. When the concave portions 21a and 22a in the drums 21 and 22 are opposed to each other, the base sheet 13 and the oxygen permeable sheet 14 are adhered to each other by thermocompression bonding only in the vicinity of the concave portions. The base sheet 13 and the oxygen permeable sheet 14 are not adhered in the portion having a length L in the concave portion, and therefore this region functions as a accommodation portion 15 that accommodates the exothermic composition 16. As described above, the filling ratio of the heat generation portions 12 must satisfy the expression (1), and such a filling ratio can be determined by selecting the area corresponding to the length L.

A thermotherapy device 1 can be obtained by cutting the sheet provided with the heat generation portions 12 into a shape desirable for the thermotherapy device 1. Second, the thus-obtained thermotherapy device 1 is sealed with an oxygen non-permeable sheet or the like. Such sealing prevents the occurrence of an oxidative reaction in the exothermic composition 16 before the thermotherapy device 1 is used.

The invention claimed is:

1. A thermotherapy device comprising a plurality of heat generation portions disposed on a flexible body having a form of a band, the plurality of the heat generation portions each comprising a base sheet and an oxygen permeable sheet forming the flexible body, an accommodation portion formed between the base sheet and the oxygen permeable sheet and having a form of a bag, and a exothermic composition that generates heat when oxidized filled in the accommodation portion, wherein the filling ratio R of the exothermic composition in the accommodation portion satisfies the expression below and is less than 0.7:

$$R \leq -0.016S + 0.94$$

wherein S is the planar area of the accommodation portion of the exothermic composition expressed in cm², and R is defined by the following expression:

R=the ratio of the mass of the exothermic composition in the accommodation portion to the maximum mass of the exothermic composition that can be filled in the accommodation portion; and the heating value of the exothermic composition in the accommodation portion is not less than 0.26 kcal/cm² per planar area of the accommodation portion.

2. A thermotherapy device according to claim 1, wherein the filling ratio R is not greater than 0.63.

3. A thermotherapy device according to claim 1, wherein the filling ratio R is not greater than 0.45.

4. A thermotherapy device according to claims 1, wherein the flexible body has a shape in the form of a flat U corresponding to the shapes of rhomboid muscle areas trapezius muscle areas and scapular muscle areas of the right and left shoulders, and the flexible body comprises at least four heat generation portions.

5. A thermotherapy device according to claim 4, wherein the heat generation portions are disposed so as to correspond to the shapes of rhomboid muscle areas, trapezius muscle areas and scapular muscle areas.

6. A thermotherapy device according to claims 1, wherein the flexible body has a shape in the form of a flat L corresponding to the shapes of rhomboid muscle areas, trapezius muscle areas or scapular muscle areas of a shoulder, and the flexible body comprises at least two heat generation portions.

7. A thermotherapy device according to claim 6, wherein the heat generation portions are disposed so as to correspond to the shapes of rhomboid muscle areas, trapezius muscle areas and scapular muscle areas.

8. A thermotherapy device according to claims 1, wherein the flexible body has a shape having a form of a band and comprises at least two heat generation portions

* * * * *